US00PP15514P2

(12) United States Plant Patent
Sato

(10) Patent No.: US PP15,514 P2
(45) Date of Patent: Feb. 1, 2005

(54) ***BEGONIA* PLANT NAMED 'GUM DROP RED'**

(50) Latin Name: *Begonia semperflorens*
Varietal Denomination: Gum Drop Red

(75) Inventor: Kazunori Sato, Tokyo (JP)

(73) Assignee: Bodger Seeds, Ltd., South El Monte, CA (US)

( * ) Notice: Subject to any disclaimer, the term of this patent is extended or adjusted under 35 U.S.C. 154(b) by 167 days.

(21) Appl. No.: 10/684,525

(22) Filed: Oct. 13, 2003

(51) Int. Cl.[7] ..... A01H 5/00
(52) U.S. Cl. ..... Plt./343
(58) Field of Search ..... Plt./343

*Primary Examiner*—Kent Bell
(74) *Attorney, Agent, or Firm*—C. A. Whealy

(57) ABSTRACT

A new and distinct cultivar of *Begonia* plant named 'Gum Drop Red', characterized by its compact, upright and uniform plant habit; freely branching growth habit, dense and bushy growth habit; green-colored leaves; freely flowering habit with numerous flowers per plant; and small mostly double flowers that are red in color and held above and beyond the foliage.

1 Drawing Sheet

Botanical classification/cultivar designation: *Begonia semperflorens* cultivar Gum Drop Red.

BACKGROUND OF THE INVENTION

The present Invention relates to a new and distinct cultivar of *Begonia* plant, botanically known as *Begonia semperflorens,* and hereinafter referred to by the name 'Gum Drop Red'.

The new *Begonia* is a product of a planned breeding program conducted by the Inventor in Fukuoka, Kyushu, Japan. The objective of the breeding program was to develop new *Begonia* cultivars with double flowers and attractive leaf and flower coloration.

The new *Begonia* originated from a cross made by the Inventor in 1995, of the *Begonia semperflorens* cultivar Double Pink, not patented, as the female, or seed parent, with the *Begonia semperflorens* cultivar Bazel, not patented, as the male, or pollen parent. The cultivar Gum Drop Red was discovered and selected by the Inventor as a flowering plant within the progeny of the stated cross in a controlled environment in Fukuoka, Kyushu, Japan.

Asexual reproduction of the new *Begonia* by cuttings taken in a controlled environment in Fukuoka, Kyushu, Japan since 1999 has shown that the unique features of this new *Begonia* are stable and reproduced true to type in successive generations.

SUMMARY OF THE INVENTION

The cultivar 'Gum Drop Red' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gum Drop Red'. These characteristics in combination distinguish 'Gum Drop Red' as a new and distinct *Begonia* cultivar:

1. Compact, upright and uniform plant habit.
2. Freely branching growth habit, dense and bushy growth habit.
3. Green-colored leaves.

4. Freely flowering habit, numerous flowers per plant.
5. Small mostly double flowers that are red in color and held above and beyond the foliage.

Plants of the new *Begonia* differ from plants of the female parent, the cultivar Double Pink, in leaf and flower coloration as plants of the cultivar Double Pink have bronze-colored leaves and pink-colored flowers. Plants of the new *Begonia* differ from plants of the male parent, the cultivar Bazel, in flower form as plants of the cultivar Bazel have single flowers.

The new *Begonia* differs from plants of the *Begonia semperflorens* cultivars Gum Drop Mandarin, disclosed in U.S. Plant patent application Ser. No. 10/684,563, Gum Drop Pink, disclosed in U.S. Plant patent application Ser. No. 10/684,531, and Gum Drop Rose, disclosed in U.S. Plant patent application Ser. No. 10/684,517, primarily in flower coloration.

The new *Begonia* can also be compared to the *Begonia semperflorens* cultivar Queen Red, not patented. However, in side-by-side comparisons conducted in Fukuoka, Kyushu, Japan, plants of the new *Begonia* differed from plants of the cultivar Queen Red in the following characteristics:

1. Plants of the new *Begonia* had smaller leaves than plants of the cultivar Queen Red.
2. Plants of the new *Begonia* had smaller flowers than plants of the cultivar Queen Red.
3. Flowers of plants of the new *Begonia* were more often double than plants of the cultivar Queen Red.
4. Flowers of plants of the new *Begonia* did not produce pollen whereas flowers of plants of the cultivar Queen Red produced pollen.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the top of the sheet comprises a side perspective view of a typical flowering plant of 'Gum Drop Red'.

The photograph at the bottom of the sheet is a close-up view of typical flowers and leaves of 'Gum Drop Red'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Lompoc, Calif. under commercial practice during the summer and fall in a polycarbonate-covered greenhouse with day temperatures about 21 to 27° C., night temperatures about 16 to 18° C. and light levels about 4,000 to 8,000 foot-candles. Unrooted cuttings were directly planted in 10-cm containers and grown for about seven weeks.

Botanical classification: *Begonia semperflorens* cultivar Gum Drop Red.

Parentage:

*Female, or seed, parent.*—*Begonia semperflorens* cultivar Double Pink, not patented.

*Male, or pollen, parent.*—*Begonia semperflorens* cultivar Bazel, not patented.

Propagation:

*Type.*—Top cuttings.

*Time to initiate roots, summer.*—About 17 days at temperatures of 25° C.

*Time to initiate roots, winter.*—About 21 days at temperatures of 23° C.

*Time to develop roots, summer.*—About 25 days at temperatures of 25° C.

*Time to develop roots, winter.*—About 32 days at temperatures of 23° C.

*Root description.*—Fibrous, fleshy, fine.

Plant description:

*Plant form.*—Compact, upright and uniform plant habit; mounded inverted triangle; freely branching with about seven lateral branches per plant; dense and bushy growth habit. Flowers are mostly double and abundant.

*Growth habit.*—Moderate growth rate, vigorous. Suitable for 10 to 15-cm containers.

*Plant height.*—About 15 cm.

*Plant width.*—About 20 cm.

*Lateral branches.*—Length: About 14 cm. Diameter: About 5 mm. Internode length: About 2.75 cm. Orientation: Mostly upright. Strength: Very strong. Texture: Smooth, glabrous. Color: 144B.

*Leaves.*—Arrangement: Simple, alternate. Length: About 7.2 cm. Width: About 6 cm. Shape: Ovate to reniform. Apex: Broadly acute. Base: Somewhat cordate to oblique. Margin: Very slightly serrate. Texture, upper and lower surfaces: Smooth, glabrous; waxy. Venation pattern: Palmate. Color: Developing leaves, upper and lower surfaces: 144A. Fully expanded leaves, upper surface: 146A. Fully expanded leaves, lower surface: 147B. Venation, upper and lower surfaces: 146B. Petiole length: About 1.5 cm. Petiole diameter: About 4 mm. Petiole texture, upper and lower surfaces: Smooth, glabrous. Petiole color, upper and lower surfaces: 144C.

Flower description:

*Flowering habit.*—Mostly double flowers with numerous tepals arranged in axillary cymes. Freely flowering habit with typically five to six flowers per cyme. Many cymes in flower simultaneously. Flowers positioned above and beyond the foliage. Flowers not fragrant. Flowers not persistent.

*Natural flowering season.*—Plants of the new *Begonia* flower year around; flowering continuous.

*Flower longevity.*—Flowers last about ten days on the plant.

*Cyme height.*—About 4 cm.

*Cyme diameter.*—About 6 cm.

*Flowers.*—Shape: Oblong. Diameter: About 2.5 by 3.5 cm. Depth (height): About 2 cm.

*Flower buds.*—Length: About 1.2 cm. Diameter: About 1.5 cm. Shape: Oval to reniform. Color: f45B.

*Tepals.*—Arrangement: Rosette. Quantity per flower: More than 50 per flower. Shape: Obovate. Apex: Obtuse. Margin: Entire to sinuate. Length, outer tepals: About 1.5 cm. Width, outer tepals: About 7 mm. Texture, upper and lower surfaces: Smooth, glabrous; velvety. Color: When opening, upper and lower surfaces: 45B to 45C. Fully opened, upper and lower surfaces: Center, 52C; towards margins, 45D; towards base, 55D to 155D.

*Flower bracts.*—Arrangement: Two, opposite. Length: About 1.6 cm. Width: About 2 cm. Shape: Reniform. Apex: Rounded. Margin: Entire. Texture, upper and lower surfaces: Smooth, glabrous. Color, upper surface: 45C. Color, lower surface: 45C to 45D.

*Peduncles.*—Length: About 3.8 cm. Diameter: About 2 mm. Strength: Strong. Texture: Smooth, glabrous. Color: 144D tinged with 45D.

*Pedicels.*—Length: About 1.5 cm. Diameter: About 1 mm. Strength: Strong, but flexible with weight of flowers. Texture: Smooth, glabrous. Color: 45D.

*Reproductive organs.*—Stamens: None observed. Pistils: Occasionally observed on individual (non-double) flowers. Pistil length: About 1.5 cm. Style length: About 4 mm. Style color: 52D. Stigma color: 12A. Ovary color: 145D.

*Seed/fruit.*—Seed and fruit production has not been observed as reproductive organs are not formed.

Disease/pest resistance: Plants of the new *Begonia* have not been observed to be resistant to pathogens and pests common to *Begonias*.

It is claimed:

1. A new and distinct cultivar of *Begonia* plant named 'Gum Drop Red', as illustrated and described.

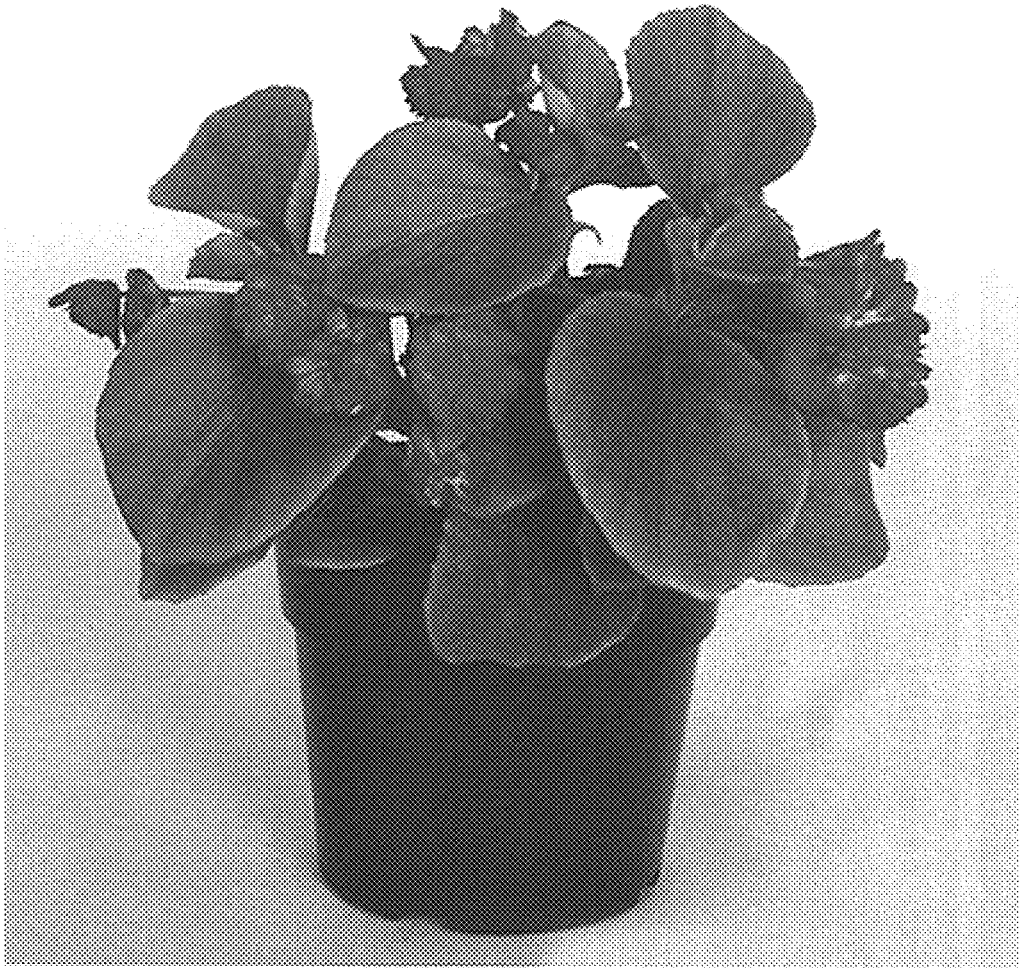
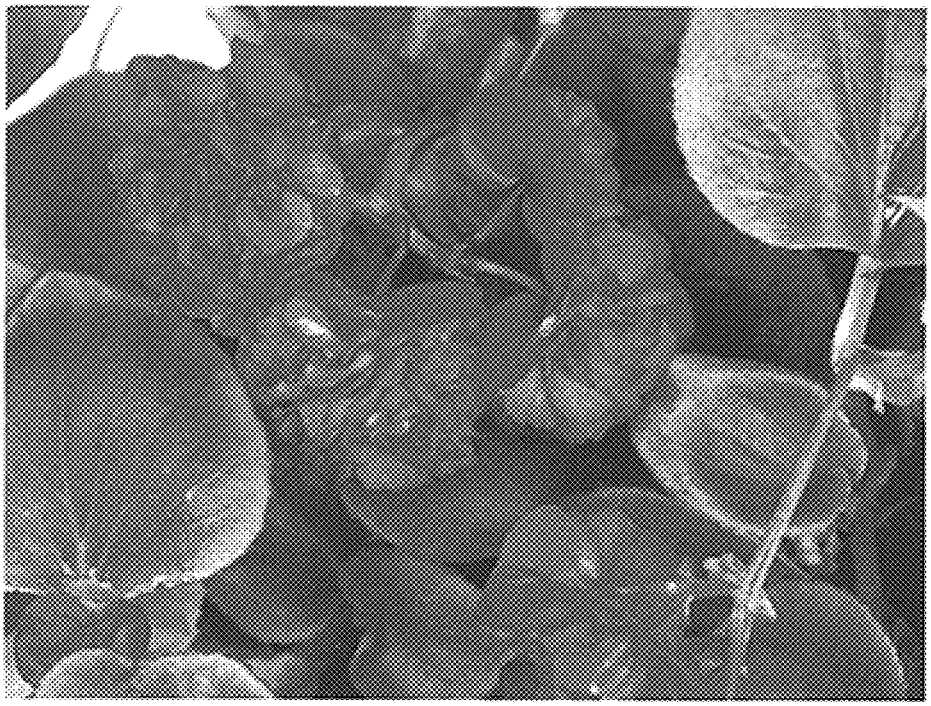

* * * * *